United States Patent
Variano et al.

(10) Patent No.: US 8,753,667 B2
(45) Date of Patent: Jun. 17, 2014

(54) MULTI-LAYERED GRADIENT VAGINAL RING

(75) Inventors: Bruce Variano, White Plains, NY (US); Jeffrey Speck, North Haledon, NJ (US); Maria Teresa Sallent, Jackson Heights, NY (US); Simone Evans, Brooklyn, NY (US)

(73) Assignee: The Population Council, Inc., New York, NY (US)

( * ) Notice: Subject to any disclaimer, the term of this patent is extended or adjusted under 35 U.S.C. 154(b) by 0 days.

(21) Appl. No.: 13/386,172

(22) PCT Filed: Apr. 7, 2010

(86) PCT No.: PCT/US2010/030183
§ 371 (c)(1),
(2), (4) Date: Feb. 27, 2012

(87) PCT Pub. No.: WO2011/011099
PCT Pub. Date: Jan. 27, 2011

(65) Prior Publication Data
US 2012/0148655 A1    Jun. 14, 2012

Related U.S. Application Data

(60) Provisional application No. 61/271,391, filed on Jul. 21, 2009.

(51) Int. Cl.
*A61K 9/00* (2006.01)
*A61K 31/57* (2006.01)
*A61K 31/565* (2006.01)
*A61P 31/18* (2006.01)
*A61P 15/18* (2006.01)
*A61M 31/00* (2006.01)
*B29C 47/00* (2006.01)

(52) U.S. Cl.
USPC ...... 424/430; 514/171; 514/177; 156/244.11; 604/285

(58) Field of Classification Search
None
See application file for complete search history.

(56) References Cited

U.S. PATENT DOCUMENTS

| | | |
|---|---|---|
| 2,541,137 A | 2/1951 | Warrick |
| 2,723,966 A | 11/1955 | Youngs |
| 2,863,846 A | 12/1958 | Tyler |
| 2,890,188 A | 6/1959 | Konkle et al. |
| 2,927,907 A | 3/1960 | Polmanteer |
| 3,022,951 A | 2/1962 | Anderson |
| 3,035,016 A | 5/1962 | Bruner |
| 3,545,439 A | 12/1970 | Duncan |
| 3,995,633 A | 12/1976 | Gougeon |
| 3,995,634 A | 12/1976 | Drobish |
| 4,012,496 A | 3/1977 | Schopflin et al. |
| 4,155,991 A | 5/1979 | Schopflin et al. |
| 4,237,885 A | 12/1980 | Wong et al. |
| 4,292,965 A * | 10/1981 | Nash et al. ............ 128/833 |
| 4,596,576 A | 6/1986 | de Nijs |
| 4,756,682 A | 7/1988 | Blaise |
| 4,822,616 A | 4/1989 | Zimmermann et al. |
| 4,922,928 A | 5/1990 | Burnhill |
| 6,126,958 A * | 10/2000 | Saleh et al. ............ 424/432 |
| 6,951,654 B2 | 10/2005 | Malcolm et al. |
| 7,824,383 B2 | 11/2010 | Sokal et al. |
| 7,833,545 B2 | 11/2010 | Ron et al. |
| 2006/0280771 A1* | 12/2006 | Groenewegen et al. ...... 424/426 |
| 2008/0286339 A1 | 11/2008 | Ron et al. |

FOREIGN PATENT DOCUMENTS

| | | |
|---|---|---|
| CN | 1899643 A | 1/2007 |
| EP | 0050867 A1 | 5/1982 |
| EP | 876815 A1 | 11/1998 |
| ES | 2171283 T3 | 9/2002 |
| GB | 798669 A | 7/1958 |
| GB | 804199 A | 11/1958 |
| JP | 51-64793 | 6/1976 |
| JP | 2007-502316 | 2/2007 |
| WO | 9702015 A1 | 1/1997 |
| WO | 02076426 A2 | 10/2002 |
| WO | 2004103336 A2 | 12/2004 |

OTHER PUBLICATIONS

Australian Search Report for Application No. 2010274946 dated Jun. 27, 2013.
International Search Report PCT/US2010/030183, dated Jul. 29, 2010.
Mordenti, J. and Chappel, W., "The use of interspecies scaling in toxicokenetics," in Toxicokinetics and New Drug Development, Yacobi et al., Eds., Pergamon Press, New York 1989, pp. 42-96.
European Examination Report for Application No. 10714730.8 dated Aug. 19, 2013.
Japanese Office Action for Application No. 2012-521631 dated Jan. 7, 2014.

* cited by examiner

*Primary Examiner* — Frederick Krass
*Assistant Examiner* — Michael P Cohen
(74) *Attorney, Agent, or Firm* — Lerner, David, Littenberg, Krumholz & Mentlik, LLP

(57) ABSTRACT

Multi-layered vaginal rings 2 comprising silicone elastomers and pharmaceutically active ingredients are disclosed. The rings comprise a number of layers, at least one of which contains a pharmaceutically active ingredient, and each of which is a silicone elastomer. The multiple layers preferably are produced from these layers of different compositions, including an inner layer 4, a middle layer 5, and an outer layer 6. After extrusion and simultaneous curing, however, the ring 2 includes a contiguous body which comprises a continuous silicone body providing unimpeded diffusion of the pharmaceutically active ingredient from the inner layer (s) 4 to the outer layer (s) 6. Methods of producing these vaginal rings and of using them are also disclosed.

16 Claims, 4 Drawing Sheets

MULTI-LAYERED GRADIENT VAGINAL RING

CROSS-REFERENCE TO RELATED APPLICATIONS

The present application is a national phase entry under 35 U.S.C. §371 of International Application No. PCT/US2010/030183 filed Apr. 7, 2010, published in English, which claims priority from U.S. Provisional Patent Application No. 61/271,391 filed Jul. 21, 2009, all of which are incorporated herein by reference.

BACKGROUND OF THE INVENTION

Vaginal devices for delivering one or more pharmaceutical actives are known.

For example, U.S. Pat. Nos. 3,995,633 and 3,995,634, describe separate, preferably spherical or cylindrical, reservoirs containing different active substances which are assembled in specially constructed holders. U.S. Pat. No. 4,237,885 describes a tube or coil of polymeric material which is divided into portions by means of a plurality of "spacers" provided in the tube, after which each of the separate tube portions is filled with a different active substance in a silicone fluid and the two ends of the tube are subsequently connected to one another. In this release system, however, transport (diffusion) of active material from one reservoir to the other takes place through the wall of the tube, especially upon prolonged storage, so that the pre-set fixed release ratio between the active substances in question will change over a period of time.

EP 0 050 867 discloses a two-layered vaginal ring which comprises a pharmacologically acceptable supporting ring covered by two layers preferably of silicone elastomers whereby the inner layer is a silicone elastomer loaded with an active substance.

U.S. Pat. No. 4,292,965 describes a ring shaped vaginal delivery system of three layers made of silicone elastomers. This patent describes in the background section different types of known intravaginal rings, and then claims to have developed an improved shell-type intravaginal ring of the type shown in FIG. 4 of the '965 patent. The layered device shown in this patent is specifically produced by methods which are described beginning at column 6, line 20 of the '965 patent. In each of these procedures, separate elastomeric rings, whether they include organopolysiloxanes or the like, are cured prior to joining with additional such layers. Thus, for example, in each case an annular core ring is cured prior to various procedures such as expansion by exposure to organic solvents to assist in layering with a further cured layer and the like. In each case, this thus leads to separate cured layers which create distinct physical junctions in the ring impeding drug diffusion through the intravaginal ring itself.

U.S. Pat. No. 4,596,576 describes a two-compartment vaginal ring wherein each compartment contains a different active substance. To achieve a suitable ring with a constant release ratio between the various active substances, the end portions of the compartments are joined by glass stoppers.

Patent Publication WO 97/02015 describes a two-compartments device, a first compartment consisting of a core, a medicated middle layer and a non medicated outer layer, and a second compartment consisting of a medicated core and a non medicated outer layer.

EP 876 815 discloses a vaginal ring which is designed for the simultaneous release of a progestogenic steroid compound and an estrogenic steroid compound in a fixed physiological ratio over a prolonged period of time. The drug delivery system comprises one compartment comprising a thermoplastic polymer core containing the mixture of the progestogenic and estrogenic compounds and a thermoplastic polymer skin, the progestogenic compound being initially dissolved in the polymer core material in a relatively low degree of supersaturation.

From the above disclosures, it is clear that e.g., the material, the layers and the compartments are all aspects of a ring device which play a role in the designs that have been developed.

SUMMARY OF THE INVENTION

In accordance with the present invention, these and other difficulties in the prior art have been overcome by the invention of a vaginal ring comprising a plurality of layers including an inner layer and an outer layer having an outer surface, each of the plurality of layers comprising a silicone elastomer, and wherein at least one of the plurality of layers comprises a pharmaceutically active ingredient, the plurality of layers comprising a continuous silicone body providing unimpeded diffusion of the pharmaceutically active ingredient from the at least one layer to the outer surface of the outer layer.

In accordance with a preferred embodiment of the vaginal ring of the present invention, the plurality of layers comprises at least three layers, including an intermediate layer between the inner layer and the outer layer.

In accordance with one embodiment of the vaginal ring of the present invention, the at least one of the plurality of layers comprises the pharmaceutically active ingredient uniformly dispersed throughout the at least one of the plurality of layers.

In accordance with a preferred embodiment of the vaginal ring of the present invention, at least two of the three layers comprises a pharmaceutically active ingredient, in which the pharmaceutically active ingredient is uniformly dispersed throughout the at least two of the three layers. In another embodiment, all three of the layers comprise a pharmaceutically active ingredient in which the pharmaceutically active ingredient is uniformly dispersed throughout the three layers.

In accordance with another embodiment of the vaginal ring of the present invention, the outer layer does not contain a pharmaceutically active ingredient.

In accordance with one embodiment of the vaginal ring of the present invention, each of the three layers may contain a different pharmaceutically active ingredient, or a combination of pharmaceutically active ingredients.

In accordance with another embodiment of the vaginal ring of the present invention, each of the three layers comprises the same pharmaceutically active ingredient.

In accordance with another embodiment of the vaginal ring of the present invention, one of the three layers comprises an estrogen alone, another of the three layers comprises a progestin alone, and another of the three layers comprises both an estrogen and a progestin.

In accordance with another embodiment of the vaginal ring of the present invention, the at least one of the plurality of layers comprises either a microbicide alone or a microbicide in combination with a progestin.

In accordance with another embodiment of the vaginal ring of the present invention, the least one of the plurality of layers comprises a PRM alone, an SERM alone, or a combination of a PRM and an SERM.

In accordance with another embodiment of the present invention, the vaginal ring has a reduced burst effect.

In accordance with the present invention, a method of manufacturing a vaginal ring has also been discovered. This method comprises manufacturing a vaginal ring having a plurality of layers comprising an inner layer and an outer layer, each of the plurality of layers comprising a silicone elastomer, and at least one of the plurality of layers comprising a pharmaceutically active ingredient, the method comprising extruding each of the plurality of layers together to form the vaginal ring and simultaneously curing each of the plurality of layers so as to provide a continuous silicone body providing unimpeded diffusion of the pharmaceutically active ingredient from the at least one layer to the outer surface of the outer layer.

In accordance with a preferred embodiment of the method of the present invention, the plurality of layers comprises at least three layers, including an intermediate layer between the inner layer and the outer layer.

In accordance with one embodiment of the method of the present invention, the extruding step comprises simultaneously extruding the plurality of layers and subsequently molding them into the form of the vaginal ring.

In accordance with another embodiment of the method of the present invention, the extruding step comprises separately extruding each of the plurality of layers which are subsequently formed into the vaginal ring.

In accordance with another aspect of the present invention, a method is provided for delivering one or more pharmaceutically active ingredients comprising inserting a vaginal ring in accordance with the present invention into the vaginal cavity of a mammal, wherein the vaginal ring is retained for a time sufficient to deliver the pharmaceutically active ingredient to the mammal.

The vaginal ring of the present invention may be designed to reduce the intensity of the burst release effect seen in other vaginal rings and/or to provide a substantially constant release rate of one or more pharmaceutically active ingredients.

A second aspect of the present invention is directed to a method of delivery of one or more pharmaceutically active ingredients using the vaginal ring described herein.

BRIEF DESCRIPTION OF THE DRAWINGS

The present invention will be more fully appreciated with reference to the following detailed description, which in turn refers to the drawings in which.

DETAILED DESCRIPTION OF THE INVENTION

Figure 1:
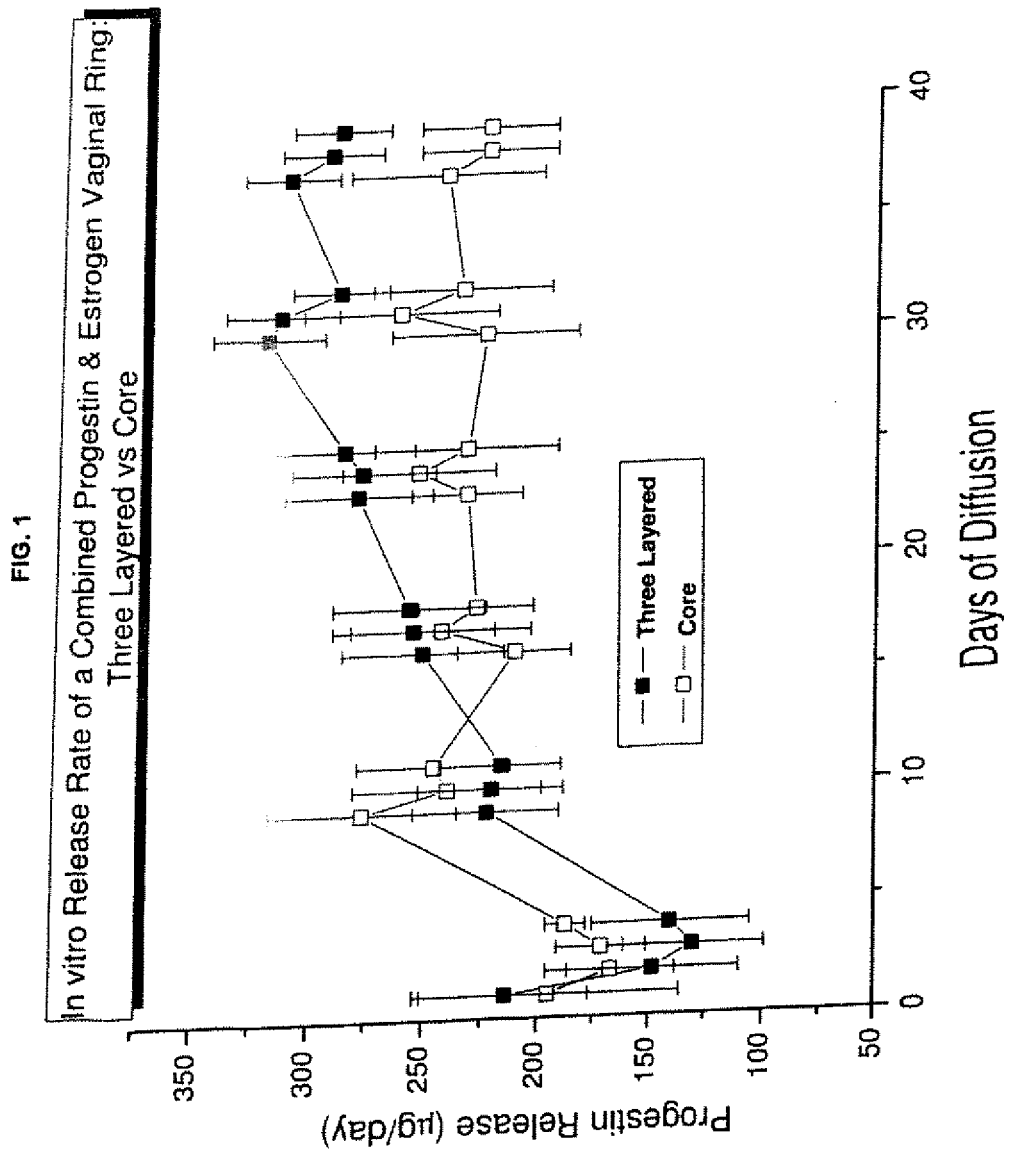
FIG. 1 is a graphical representation of the progestin release rate of a combined progestin and estrogen vaginal ring in accordance with the present invention.

In the present specification, the term "multi-layered vaginal ring" is used. The multi-layered or three-layered preferred embodiment of the vaginal ring of the present invention is referred to in that manner because during preparation the ring includes separate discreet layers. However, as will be made clear in this specification, when the ring is finally prepared, and the various layers originally utilized are brought into contact and simultaneously cured, since the individual layers will then form into a single contiguous solid body, they no longer include separate "layers" as used in the conventional sense. At that point, the single ring matrix includes individual layers to the extent that there are areas of the ring which include different concentrations of drugs or other components therein.

The present invention is a multi-layered vaginal ring drug delivery system constructed of silicone elastomer allowing for effective simultaneous release of one or more pharmaceutically active ingredients. Preferably, this invention is such a three-(or more) layered vaginal ring drug delivery system constructed of silicone elastomers.

The layered construction of this vaginal ring allows for a gradient to be established within the vaginal ring. The layered construction can allow for a reduced burst-release effect as compared to other vaginal rings. The layered construction can also allow for a more constant rate release of active ingredient as compared to other vaginal rings. In addition, a multilayered motif allows for the delivery of more than one pharmaceutically active ingredients. This device could be adapted for multiple delivery functions as well where vaginal transmission is the preferred route.

By virtue of the specific method by which the vaginal ring of the present invention is produced, it has a structure which is unique as compared to the prior art, which thus leads to possession of properties not obtainable with any such devices in the prior art. In particular, the layered construction of the vaginal rings of the present invention comprises a continuous silicone body irrespective of the layers defining that structure. This thus permits for unimpeded diffusion of pharmaceutically active ingredients through the layers of this device, and at the same time permits the individual layers to include different active pharmaceutical ingredients, or to be devoid of any pharmaceutical ingredients, or in any event, even where more than one layer includes the same pharmaceutical ingredient, the device still permits for a constant release rate of that active ingredient through the device and into the patient, particularly as compared to what was previously possible with such devices.

All of this is now achievable by applicants' having devised a method for producing such a device; namely, one in particular in which each of the multiple layers, and preferably at least three such layers, is extruded into the form of the vaginal ring, and then after the entire ring has been produced, the layers are simultaneously cured. Thus, whether the layers are separately extruded into the final product, or simultaneously co-extruded into the final product, they are only cured after the product has been molded into its final form. It has thus been unexpectedly discovered that by doing so the unique structure of the present invention is now achievable, and the unexpected results of having that structure can now be realized.

The vaginal ring 2 of the invention (see FIG. 4) is preferably prepared from at least three distinct layers of varying or similar thickness (4.0-10.0 mm in cross-sectional diameter and 40-70 mm in overall diameter), each of the three layers comprising a silicone elastomer. All layers are comprised of either similar silicone rubbers or of silicone rubbers that can vary chemically one from the other, such as fluorosilicone or silicones with differing alkyl pendant groups.

At least one layer of the ring is loaded with a pharmaceutically active ingredient. In some embodiments, two layers contain a pharmaceutically active ingredient. In other embodiments, three layers contain a pharmaceutically active ingredient. In embodiments where the ring contains a pharmaceutically active ingredient in more than one layer, the pharmaceutically active ingredient may be the same in each layer, or may be different in each layer, at the same or varying doses. Additionally, the ring may contain two layers containing the same pharmaceutically active ingredient, with a third layer containing a different pharmaceutically active ingredient, once again with the same or varying doses.

The vaginal ring of the present invention may contain up to three pharmaceutically active ingredients with all pharmaceutically active ingredients in the crystalline phase.

In any event, with respect to any layer or layers of a vaginal ring in accordance with the present invention which does contain a pharmaceutically active ingredient, it is preferred that the pharmaceutically active ingredient be uniformly dispersed throughout that particular layer or layers. This is generally accomplished by thoroughly mixing the active ingredient with the silicone elastomer.

The ring may also comprise one or more inert layers containing no pharmaceutically active ingredient. In certain embodiments, the ring contains an inert, outer layer. This inert outer layer prevents micro pitting at the surface of the ring. In certain embodiments, the ring 2 consists of three layers, the innermost layer 4 and middle layer 5 containing a pharmaceutically active ingredient, and the outermost layer 6 devoid of a pharmaceutically active ingredient. In other embodiments, the ring contains more than one inert layer containing no pharmaceutically active ingredient.

Figure 4:
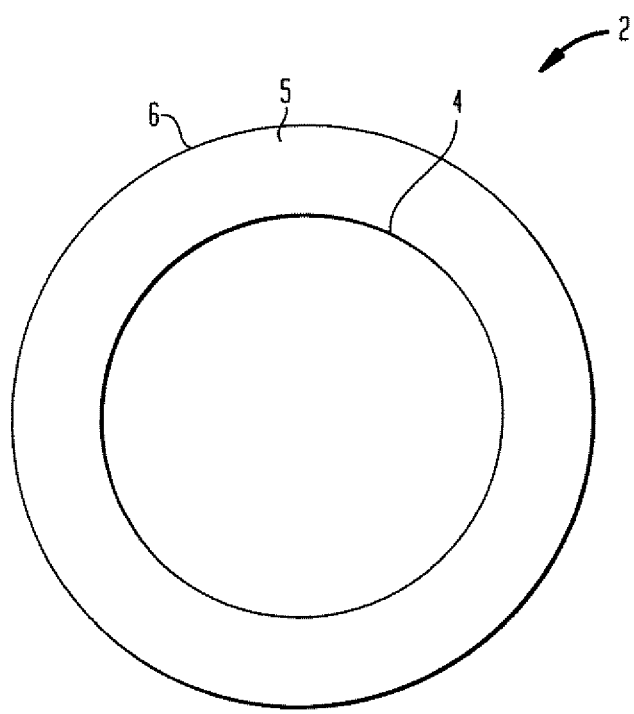
FIG. 4 is a top, elevational view of a vaginal ring in accordance with the present invention.

In any event, in each of these embodiments the preferred procedure for producing this product is essentially the same. Thus, with the preferred three-layered composition of the present invention, three distinct drug-silicone elastomer batches, with various drug concentrations (possibly including zero) are prepared for each layer of the vaginal ring. First, the drug substance and the silicone elastomer are premixed, prior to extrusion. Then, secondly, all three drug/silicon elastomer batches are placed in one or more extruders and they are then simultaneously extruded. Third, the extruded material is placed into ring molds and heated to the required curing temperatures for a period of time selected so as to form a continuous ring with no intervening boundary layers. It is in this manner that an essentially solid, contiguous, matrix-type body is produced from the three layers, and unimpeded diffusion of the drug components is now obtained. Thus, while the vaginal ring 2 of the present invention will now appear to have a single layer, as shown in FIG. 4, it actually has three separate areas of different compositions, since it was prepared from the separate layers in the manner discussed above.

A variety of physiologically acceptable resins or elastomers have been disclosed in the literature as being suitable for making vaginal rings, including silicone elastomers such as polyorganosiloxanes, e.g., polydimethylsiloxane or a copolymer of dimethylsiloxane and methylvinylsiloxane, conventional silicone rubber, polyurethanes, SILASTIC 382 (Dow Corning), latex rubber, polyamides, polyesters, polytetrafluoroethylene, polyethylene vinyl acetate and nylon. The vaginal rings of the present invention preferably contain silicone elastomers, and more preferably silicone rubbers such as medical grade organopolysiloxanes, such as among the following:

1. Organopolysiloxanes to be vulcanized with peroxide curing catalysts, e.g., benzoyl peroxide or di-p-chlorobenzoyl peroxide at temperatures of about 200° C. and requiring a heat after-treatment, e.g., those described in U.S. Pat. Nos. 2,541,137; 2,723,966; 2,863,846; 2,890,188 and 3,022,951.
2. Hydroxyl-terminated organopolysiloxanes of the RTV (room temperature vulcanizing) type which harden to elastomers at room temperature after the addition of cross-linking agents in the presence of curing catalysts and under the atmospheric humidity. Typical curing catalysts are metallic salts of carboxylic acids, preferably tin salts, e.g., tin (II) octoate and tin (II)-2-ethylhexanoate.
3. Single-component silicone rubber compositions which are cured at room temperature under atmospheric humidity without any further additives. These single component compositions contain primarily organopolysiloxanes with two terminal-positioned hydrolyzable acyloxy groups, e.g., acetoxy; the acyloxy groups are hydrolyzed under atmospheric humidity to form trifunctional siloxane units which crosslink the polymer into a cured elastomer. Such organopolysiloxanes are described, e.g., in U.S. Pat. Nos. 2,927,907 and 3,035,016 and in British Patents 798,669 and 804,199.
4. Two-component dimethylpolysiloxane compositions, platinum-catalyzed at room temperature or at elevated temperature and capable of addition cross-linking. The medicated and/or non-medicated layers can be constructed from an elastomer selected from classes 1 to 4 above.

The dimensions of the vaginal rings of the present invention can be determined by persons skilled in the art using standard techniques. In general, the vaginal ring typically has an overall diameter of about 40 mm to about 70 mm, preferably from 54 mm to 60 mm. The overall cross sectional diameter of the ring generally ranges from about 4 mm to about 10 mm, and preferably from about 6 mm to about 9 mm. Thus, the thickness of each layer generally ranges from about 0.5 mm to about 9 mm. Each layer may have the same or different thicknesses. The thickness of the outer layer 6 affects the distance the drugs in the inner layer(s) 4 and middle layer(s) 5 must travel in order to reach the vaginal tissues. Thus, it can be varied to control the release rate of the drug from the middle and inner layers.

The vaginal rings of the present invention may be prepared by first mixing or dispersing the drug in the elastomer, e.g., to form a matrix. Once the drug is mixed with the matrix material to achieve a substantially uniform dispersion, the desired shape of the resultant dispersion is achieved by molding, casting, extrusion, or other appropriate process. For example, the dispersion may be prepared by a method which involves co-extrusion. In this method, the layers of elastomer, at least one of which contains the drug, are co-extruded and then cured by heating at a temperature below the melting point of the drug.

This vaginal ring can be manufactured either by mono extrusion of each layer followed by assembly with the appropriate techniques and then curing of the multiple layers, or by co-extrusion of all of the layers, including the three-layer embodiment, with simultaneous construction of the ring body, again followed by curing of all of the layers simultaneously. In addition, one may mono-extrude or co-extrude chemically differing silicone elastomers such as fluorosilicone or siloxanes with varying pendant groups, thus allowing for unique combinations of pharmaceutically active ingredient and silicone matrices.

In certain embodiments, all three layers contain the same pharmaceutically active ingredient. In other embodiments, the ring contains two different pharmaceutically active ingredients. In still other embodiments, the ring contains three different pharmaceutically active ingredients, or one or more of the layers includes a combination of a pharmaceutically active ingredient which is contained in at least one other layer and a different pharmaceutically active ingredient, which may or may not be contained in at least one other layer.

The concentration of active in each layer may be the same or may be different. For example, the concentration may be lower in the outermost layer, with a higher concentration in the middle layer, and a still higher concentration in the innermost layer. In some embodiments, the concentration of active is the same in two layers, but differs in the third layer. As an example, progesterone can be utilized as the following varying concentrations: 3% drug loading in the outer layer; 19% drug loading in the muddle layer; and 60% drug loading in the innermost layer.

The concentration of drug in each layer varies by the physicochemical properties of the pharmaceutically active ingredient. Typical drug concentrations are from 0.1% to 60%.

By manufacturing the vaginal ring of the present invention in a multilayered fashion with a different concentration of the first pharmaceutically active ingredient, such as estrogen, in one or more layers, it is possible to deliver this first pharmaceutically active ingredient effectively from the silicone body along with the second pharmaceutically active ingredient (such as a progestin such as 19-norprogestin) in a separate or combined layer inside the ring body. This improvement in design allows for a lower and constant release of the first pharmaceutically active ingredient from the ring body with a potential for improving the safety profile of this device (decreased incidence of clotting such as deep vein thrombosis) over prior similar implements.

The one or more pharmaceutically active ingredients can be any appropriate ingredient which can be delivered vaginally and includes steroids, hormones, contraceptives, estrogens, progestins, selective estrogen receptor modulators (SERMs), progesterone receptor modulators (PRMs), anti-virals, anti-retrovirals (including non-nucleoside reverse transcriptase inhibitors (NNRTI)), chemotherapeutic agents such fluorouracil, anti-microbials such as anti-fungals, anti-bacterials or anti-protozoals.

Estrogens include estradiol valerate, estradiol benzoate, 17-β estradiol, estradiol cypionate, estrone, piperazine estrone sulfate, estriol, ethyl estradiol, polyestradiol phosphate, estrone potassium sulfate, benzestrol, chlorotrianisene, methallenestril, dienestrol, diethylstilbestrol diphosphate, mestranol, diethylstilbestrol (DES), quinestranol, phytoestrogens, animal-derived estrogens (e.g., equine estrogens), and metabolic derivatives of animal-derived estrogens.

Progestins include progesterone, nestorone, nomegestrol acetate, drospirenone, dienogest, trimegestone, 17-hydroxy progesterone derivatives, 19-nor-testosterone derivatives, 19-nor-progesterone derivatives norethindrone, norethindrone acetate, norethynodrel, norgestrel, norgestimate, ethynodiol diacetate, allylestrenol, lynoestrenol, fuingestanol acetate, medrogestone, norgestrienone, dimethiderome, ethisterone, cyproterone levo-norgestrel, dl-norgestrel, cyproterone acetate, gestodene, desogestrol, dydrogesterone, ethynodiol diacetate, medroxyprogesterone acetate, megestrol acetate, phytoprogestins, animal-derived progestins, and metabolic derivatives of animal-derived progestins.

Steroids include androgens such as testosterone, methyltestosterone, fluoxymesterone, testosterone cypionate, testosterone enanthate, testosterone propionate, oxymetholone, ethylestrenol, oxandrolone, nandrolone phenpropionate, nandrolone decanoate, testosterone buccilate, stanozolol, dromostanolone propionate, androstenedione, dehydropepiandrosterone, dehydroepiandrosterone sulfate (DHEAS), dihydrotestosterone, phytoandrogens, animal-derived androgens, and metabolic derivatives of animal-derived androgens.

Estrogen receptor modulators include tamoxifen, raloxifene, clomiphene, droloxifene, idoxifene, toremifene, tibolone, ICI 182,780, ICI 164,384, diethylstilbesterol, genistein, nafoxidine, moxestrol, 19-nor-progesterone derivatives, and 19-nor-testosterone derivatives.

Progestin receptor modulators include RU486, CDB/VA 2914 (ulipristal acetate), 19-nor-progesterone derivatives, 19-nor-testosterone derivatives, 6-aryl-1,2-dihydro-2,2,4-trimethylquinoline derivatives, 5-aryl-1,2-dihydro-5H-chromeno[3,4-f]quinoline derivatives, 5-alkyl 1,2-dihydrochomeno[3,4-f]quinoline derivatives, and 6-thiophenehydroquinoline derivatives.

In certain embodiments, the ring contains both an estrogen and a progestin, or a progestin alone. Rings of this type are especially suitable for contraception. In other embodiments, the ring contains a microbicide alone. Rings of this type are especially suitable as protection against HIV/AIDS. In other embodiments, the ring contains both a progestin and a microbicide. Rings of this type are especially suitable for dual purposes in protection against HIV/AIDS and for contraception. In other embodiments, the ring contains both a SERM and a PRM, or a PRM alone or a SERM alone. Rings of this type may be suitable for the treatment of fibromas.

Dosages and desired drug concentrations of the pharmaceutical compositions of the present invention may vary depending on several factors, including the potency of the pharmaceutically active ingredient. The appropriate dosage is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" in *Toxicokinetics and New Drug Development*, Yacobi et al., Eds., Pergamon Press, New York 1989, pp. 42-96. Amounts of the drug generally range from about 0.1 mg to about 300 mg/day. In some embodiments, the amount generally varies from about 0.5 to about 50 mg/day. In some other embodiments, the amount generally varies from about 10 mg/day to about 200 mg/day, and in others, the amount generally varies from about 10 mg/day to about 50 mg/day.

Depending on active ingredient, the ring of the present invention can be used as a contraceptive, for hormone replacement therapy, as a microbicide preventative (including anti-retroviral compounds for HIV prevention), for fibroma treatment and/or as a dual protection device for human females.

The ring or device is inserted into the vaginal cavity and retained therein for a desired period of time for administration of the pharmaceutically active compounds incorporated into the device.

The present invention also includes a method of delivering one or more pharmaceutically active ingredients, comprising inserting a ring described herein into the vaginal cavity of a mammal, wherein the ring is retained for time sufficient to deliver the pharmaceutically active ingredient(s) to the mammal.

EXAMPLES

Example 1

Mono Extrusion

For manufacture of this vaginal ring Parts A and B of the appropriate silicone elastomer are combined onto a roll-mill until completely flat. The drug load is then mixed separately with an emulsifying excipient. Next, the emulsified drug load is spread onto the silicone sheet of a certain thickness and placed in the roll-mill until it is thinned out. The process above is repeated for the other layers that will comprise the ring; in so doing different silicone and/or pharmaceutically active ingredients can be used as needed.

Each layer is placed into an extruder and molded into the appropriate shape. These shaped silicone/pharmaceutically active ingredient matrices are assembled with the appropriate techniques into a ring and vulcanized according to procedure, resulting in the finished vaginal ring.

Example 2

Co-Extrusion

With co-extrusion there is a simultaneous extrusion bringing both elements together by way of a manifold apparatus. In so doing a multilayered structure can be assembled in one step. An example of such a device is described in U.S. Pat. No. 4,756,682.

For assembly of the vaginal ring described in this document the silicone/pharmaceutically active ingredient layers described in Example 1 are fed into the extruder apparatus with manifold attachment simultaneously and extruded and combined in one step.

Example 3

In Vitro Release Rates

For this example, vaginal rings made of silicone elastomer and drug was prepared by monoextrusion. For the 19-norprogestin/estradiol ring, 7.9% by weight 19-norprogestin was present in the inner layer, and 2.5% by weight estradiol was present in the middle layer. The outer layer contained no drug. For the progesterone ring, the drug was present in both the inner and middle layers, with the outer layer containing no drug. The inner layer contained 25% by weight of progesterone, and the middle layer contained 12% by weight progesterone. The polymer used in all of the layers was silicone elastomer.

For purposes of comparison, vaginal ring products were prepared which did not include the drug component in a three-layered vaginal ring product. In a first comparative vaginal ring product, a "core" was produced having a cured silicone rod containing the active pharmaceutical ingredient, which was manufactured entirely separately from the vaginal ring body itself. The ring body was produced by injecting silicone into a mold which provided for the formation of a channel within the ring body. The core itself, containing the drug, was molded in a separate step by injecting the silicone/drug mixture into an appropriately configured mold, and allowing it to cure. The cured silicone rod is then inserted into channels within the ring body during the final phase of manufacture, and then sealed with a medical adhesive. In the specific embodiment referred to in FIGS. 1 and 2, the "core" product included 12% by weight estrogen and 7.9% of the progestin (19-norprogestin). In a second comparative vaginal ring product, a "matrix" was produced in which the drug component was uniformly dispersed in a single ring. The silicone containing the dispersed drug was then injected into a ring mold and allowed to cure. In the specific embodiment referred to in FIG. 3, the "matrix" product included 20% by weight of progesterone.

The rate of both 19-norprogestin and estradiol (E2) release from each of the vaginal rings, including the three-layered rings of the present invention, and the comparative "core" and "matrix" rings, was determined in vitro by suspending the rings in a 500 mL sealed PTFE bottle with an appropriate elution medium. The sample bottles were subsequently agitated in a heated shaking water bath set at 37° C. with a one inch stroke and 100 cycles per minute. The elution medium consisted of double-distilled water.

Samples of the elution medium were taken every 24 hours and simultaneously analyzed for released 19-norprogestin and E2. After sampling, the elution medium was changed and the sample bottle placed back into the shaking water bath.

Turning first to FIG. 1, this is a comparison of the three-layered product including both a progestin and an estrogen compound as described in ¶ [0066] hereinabove with a core-containing ring utilizing a cured silicone rod also containing 7.9% by weight 19-norprogestin and 12% by weight estradiol. As shown in FIG. 1, progestin release was measured over time, and the data clearly demonstrate that, with the three-layered ring of the present invention with comparable amounts of the drug, there is a greater range of drug release as compared to that of the core material with which it is compared. This, of course, is wholly apart from the fact that with the three-layered product of the present invention there is the added advantage of the potential for delivering more than one drug ingredient at either the same, similar, or different release levels. Furthermore, it is possible to deliver more than one drug without cross-interference from the other drug.

Figure 2:
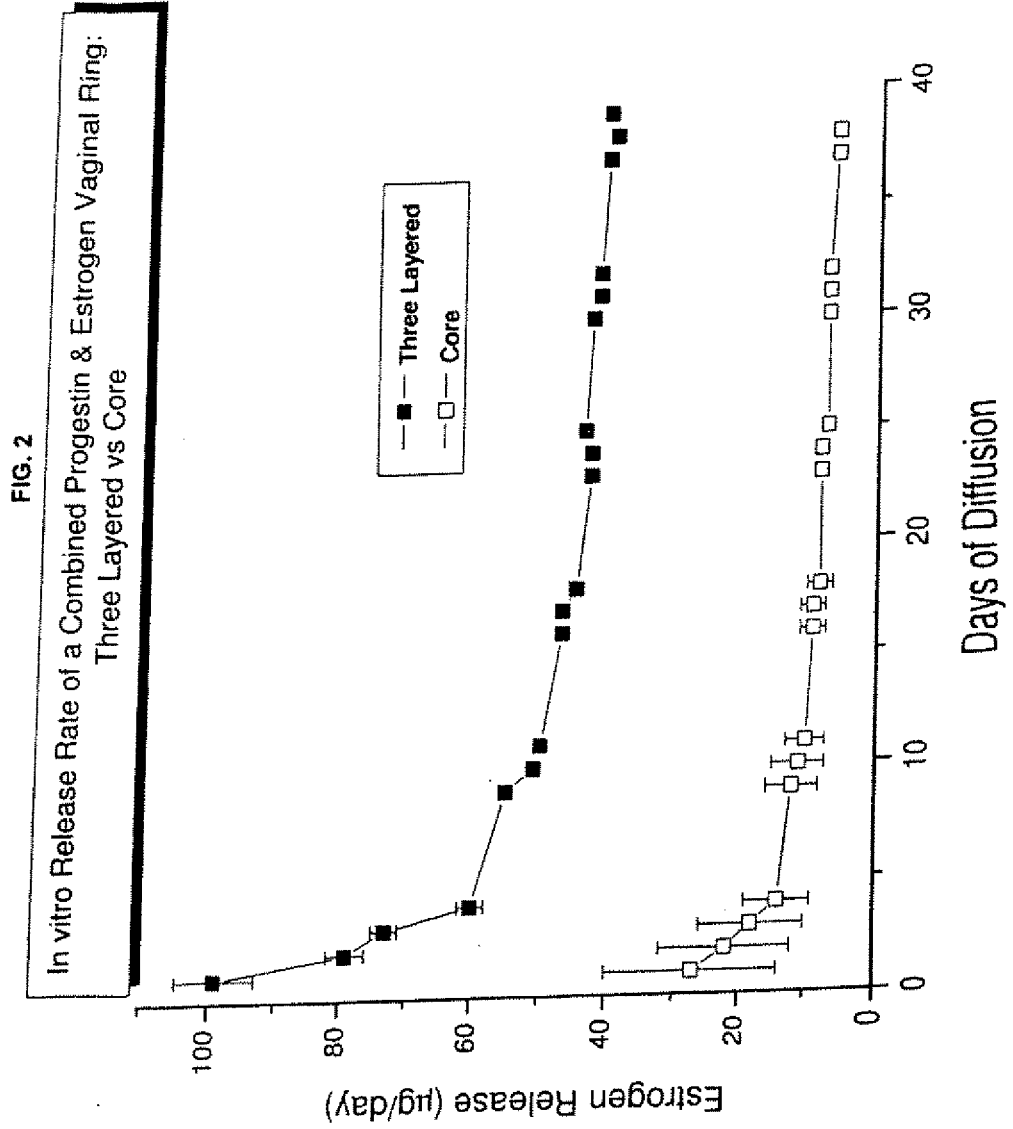
FIG. 2 is a graphical representation of the estrogen release rate for a vaginal ring in accordance with the present invention including combined progestin and estrogen.

Turning to FIG. 2, estrogen release was measured, and once again, as was the case with progestin release shown in FIG. 1, the three-layered product of the present invention clearly demonstrates a far greater range of drug release versus the core product thereof. Indeed, even though the "core" ring product included more of the estrogen component (12% vs. 2.5% in the three-layered ring), the results unexpectedly demonstrated that the three-layered ring of the present invention was capable of delivering the drug at similar or even higher rates even with less total drug load. It is noted in this regard that the total amount of drug in each layer will not be an accurate reading of the weight percent of drug in the overall ring itself, since in a multi-layered ring each of the concentric rings will have a different circumference, and thus a different weight. That, in turn, will effect the weight percent of the drug in the overall ring. However, for the purposes of the examples herein, the weight percentages have been selected to provide the comparable results discussed herein and shown in the Figures.

Figure 3:
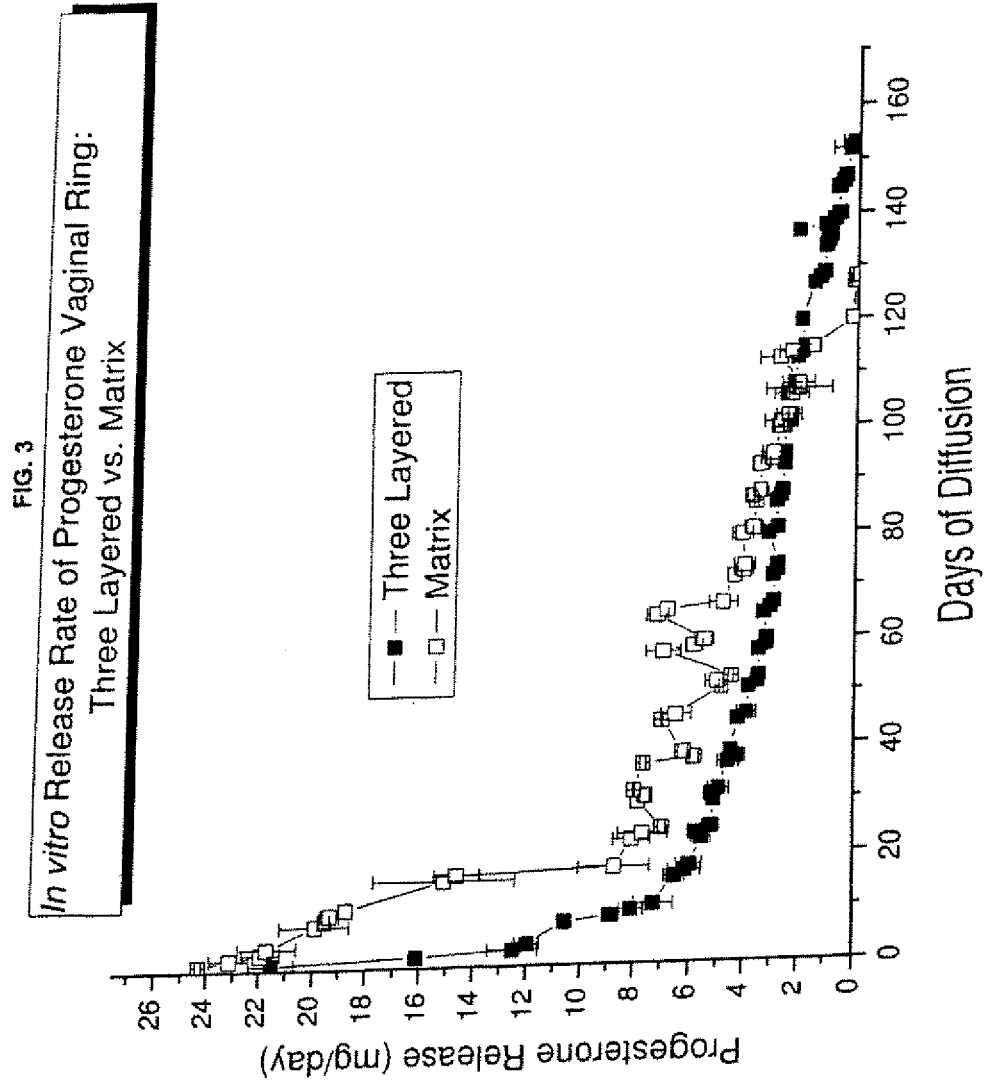
FIG. 3 is a graphical representation of the release rate of progesterone for a vaginal ring in accordance with the present invention as compared to the matrix composition ring.

Turning to FIG. 3, in this case the three-layered composition containing only progesterone, as set forth in ¶ [0066] above, was compared to a matrix product which also included a total of 20% by weight progesterone therein. As can be seen in FIG. 3, using the three-layered composition of the present invention, the release of the drug is more controlled and consistent than with the matrix product with which it is compared, and furthermore the initial burst effect is significantly diminished in connection with the three-layered ring as compared to this matrix product.

All patent and non-patent publications cited in this specification are indicative of the level of skill of those skilled in the art to which this invention pertains. All these publications and patent applications are herein incorporated by reference to the same extent as if each individual publication or patent application was specifically and individually indicated as being incorporated by reference herein.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A vaginal ring comprising a plurality of layers including at least an inner layer and an outer layer having an outer surface, each of said plurality of layers comprising a silicone elastomer, and at least one of said plurality of layers comprising a pharmaceutically active ingredient, said plurality of layers comprising simultaneously cured layers which have been co-extruded and cured at a temperature below the melting point of said pharmaceutically active ingredient, thereby providing a continuous silicone body providing unimpeded diffusion of said pharmaceutically active ingredient from said inner layer(s) to said outer surface of said outer layer.

2. The vaginal ring of claim 1 wherein said plurality of layers comprises at least three layers, including an intermediate layer between said inner layer and said outer layer.

3. The vaginal ring of claim 2 wherein at least two of said at least three layers comprise a pharmaceutically active ingredient uniformly dispersed throughout at least two of said at least three layers.

4. The vaginal ring of claim 3 wherein each of said at least three layers comprises a pharmaceutically active ingredient uniformly dispersed throughout each of said at least three layers.

5. The vaginal ring of claim 4 wherein each of said at least three layers contains a different pharmaceutically active ingredient or a combination of pharmaceutically active ingredients.

6. The vaginal ring of claim 5 wherein one of said at least three layers comprises an estrogen alone, another of said at least three layers comprises a progestin alone, and another said at least three layers comprises both an estrogen and a progestin.

7. The vaginal ring of claim 4 wherein each of said at least three layers comprises the same pharmaceutically active ingredient.

8. The vaginal ring of claim 1 wherein said pharmaceutically active ingredient is uniformly dispersed throughout said at least one of said plurality of layers.

9. The vaginal ring of claim 1 wherein said outer layer does not contain a pharmaceutically active ingredient.

10. The vaginal ring of claim 1 wherein said at least one of said plurality of layers comprises a microbicide alone or a microbicide in combination with a progestin.

11. The vaginal ring of claim 1 wherein said at least one of said plurality of layers comprises a progesterone receptor modulator alone, an selective estrogen receptor modulator alone, or a combination of a progesterone receptor modulator and an selective estrogen receptor modulator.

12. A method of manufacturing a vaginal ring comprising a plurality of layers including an inner layer and an outer layer having an outer surface, each of said plurality of layers comprising a silicone elastomer, and at least one of said plurality of layers comprising a pharmaceutically active ingredient, said method comprising extruding each of said plurality of layers into the form of said vaginal ring, and simultaneously curing each of said plurality of layers at a temperature below the melting point of said pharmaceutical active ingredient so as to provide a continuous silicone body providing unimpeded diffusion of said pharmaceutically active ingredient from said inner layer(s) to said outer surface of said outer layer.

13. The method of claim 12 wherein said plurality of layers comprises at least three layers, including an intermediate layer between said inner layer and said outer layer.

14. The method of claim 12 wherein said extruding step comprises simultaneously extruding said plurality of layers into the form of said vaginal ring.

15. The method of claim 12 wherein said extruding step comprises separately extruding each of said plurality of layers into the form of said vaginal ring.

16. A method of delivering one or more pharmaceutically active ingredients comprising inserting the vaginal ring of claim 1 into the vaginal cavity of a mammal, wherein said vaginal ring is retained for a time sufficient to deliver said pharmaceutically active ingredient to said mammal.

* * * * *

UNITED STATES PATENT AND TRADEMARK OFFICE
CERTIFICATE OF CORRECTION

PATENT NO. : 8,753,667 B2  
APPLICATION NO. : 13/386172  
DATED : June 17, 2014  
INVENTOR(S) : Variano et al.

Page 1 of 1

It is certified that error appears in the above-identified patent and that said Letters Patent is hereby corrected as shown below:

In the Claims  
Column 11, line 26, delete "4" and insert therefor --2--.  
Column 11, line 35, delete "4" and insert therefor --2--.

Signed and Sealed this  
Ninth Day of February, 2016

Michelle K. Lee  
*Director of the United States Patent and Trademark Office*